(12) United States Patent
Devary et al.

(10) Patent No.: US 8,071,716 B2
(45) Date of Patent: Dec. 6, 2011

(54) THYMUS-SPECIFIC PROTEIN

(75) Inventors: Yoram Devary, Jerusalem (IL); Uziel Sandler, Jerusalem (IL)

(73) Assignee: Immune System Key Ltd., Jerusalem (IL)

( * ) Notice: Subject to any disclaimer, the term of this patent is extended or adjusted under 35 U.S.C. 154(b) by 913 days.

(21) Appl. No.: 11/666,123

(22) PCT Filed: Oct. 26, 2005

(86) PCT No.: PCT/IL2005/001113
§ 371 (c)(1),
(2), (4) Date: May 31, 2007

(87) PCT Pub. No.: WO2006/046239
PCT Pub. Date: May 4, 2006

(65) Prior Publication Data
US 2009/0018060 A1    Jan. 15, 2009

Related U.S. Application Data

(60) Provisional application No. 60/621,086, filed on Oct. 25, 2004.

(51) Int. Cl.
*A61K 38/00* (2006.01)
*C07K 4/12* (2006.01)

(52) U.S. Cl. .......... 530/300; 530/326; 530/324; 514/1.1

(58) Field of Classification Search .......... None
See application file for complete search history.

(56) References Cited

FOREIGN PATENT DOCUMENTS
| WO | 98/01557 | 1/1998 |
| WO | 01/77137 A1 | 10/2001 |
| WO | 2004/005318 A2 | 1/2004 |

OTHER PUBLICATIONS

Harris, et al. (1994). *Three distinct human thymopoietins are derived from alternatively spliced mRNAs*. Proceedings of the National Academy of Sciences of the United States of America, vol. 91, No. 14, 1994, pp. 6283-6287, XP-002379435.

DATABASE UniProt, Aug. 1, 1998, "Integral membrane acetyltransferase." XP-002379438, retrieved from EBI accession No. UANIPROT:066257.

DATABASE EMBL, Dec. 14, 1999, "Human DNA sequence from clone RP11-481H12 on chromosome 10 Contains a FK506 binding protein 1B (FKBP1B) pseudogene." XP-002379439, retrieved from EBI accession No. EM PRO:AL133482.

Nakano, et al. (1998). "A gene cluster for 6-deoxy-l-talan synthesis in *Actinobacillus actinomycetemcomitans*" Biochimica et Biophysica acta. Gene Structure and Expression, Elsevier, Amsterdam, NL, Vo. 1442, No. 2-3, pp. 409-414, XP004275282.

Federico, M.D. et al. (1995). *Effects of thymostimulin with combination chemotherapy in patients with aggressive non-hodgkin's lymphoma*. Am. J. Clin. Oncol. 18(1) pp. 8-14.

Azizi, et al. (1984). *Postsurgical adjuvant treatment of malignant melanoma patients by the thymic factor thymostimulin*. Arzneim.-Forsch./Drug Res 34(II), Nr. 9, pp. 1043-1046.

Iaffaioli, et al. (1988). *Effect of thymic extract 'thymostimulin' on the incidence of infections and myelotoxicity during adjuvant chemotherapy for breast cancer*. Thymus 12: 69-75.

Schulof, et al. (1985). *A randomized trial to evaluate the immunorestorative properties of synthetic thymosin-$\alpha_1$ in patients with lung cancer*. Journal of Biological Response Modifiers 4:147-158.

Gonnelli, et al. (1995). *Thymostimulin in association with chemotherapy in breast cancer patients with bone metastases*. Cln. Drug Invest. 9(2), pp. 79-87.

Mustacchi, et al. (1994). *High-dose folinic acid (FA) and fluorouracil (FU) plus or minus thymostimulin (TS) for treatment of metastatic colorectal cancer: results of a randomized multicenter clinical trial*. Anticancer Research 14: 617-620.

Periti, et al. (1993). *Antimicrobial chemoimmunoprophylaxis in Colorectal Surgery with Cefotetan and thymostimulin: prospective, controlled multicenter study*. Journal of Chemotherapy. vol. 5,1, pp. 37-42.

*Primary Examiner* — Daniel C Gamett
(74) *Attorney, Agent, or Firm* — The Nath Law Group; Susanne M. Hopkins

(57) ABSTRACT

The invention provides the novel thymus-specific human protein T101, an 84-amino acid polypeptide isolated from the human thymus. The full T101 peptide contains a 33-amino acid signal peptide and a 51-amino acid T101 peptide sequence with both immune stimulatory and inhibitory activities. Also provided are modified peptides and partial T101 peptide sequences.

18 Claims, 9 Drawing Sheets

```
5002  atgatggcactcagagaagccaggggctcatgttacccagagctgc
       M  M  A  L  R  S  Q  G  L  M  L  P  Q  S  C
5047  ccacaactggctttcctcacctagtgccttggcagcagtgtct
       P  Q  L  A  F  L  T  L  S  A  L  A  A  V  S
5092  ttttcagctctgcatctctgcttagtggggagccagtccagagc
       F  S  A  L  H  L  W  L  S  G  E  P  V  Q  S
5137  tctggaacaaaggacatgagatccaagatccgattccaagcgagtg
       S  G  T  K  D  M  R  S  K  S  D  S  K  R  V
5182  agtgacaagcagctaatttccaaagctgtgtggtggacattttt
       S  D  K  Q  L  I  S  K  A  V  W  W  T  F  F
5227  cttccttcaaccctctggggagagaaaatga 5256
       L  P  S  T  L  W  E  R  K  *
```

FIG.1

SEQUENCE LISTING

<160> NUMBER OF SEQ ID NOS: 20

<210> SEQ ID NO 1
<211> LENGTH: 255
<212> TYPE: DNA
<213> ORGANISM: Homo sapiens

<400> SEQUENCE: 1

```
atgatggcac tcagaagcca ggggctcatg ttaccccaga gctgcccaca actggctttc      60
ctcaccctaa gtgccttggc agcagtgtct ttttcagctc tgcatctctg gcttagtggg     120
gagccagtcc agagctctgg aacaaaggac atgagatcca aatccgattc caagcgagtg     180
agtgacaagc agctaatttc caaagctgtg tggtggacat tttttcttcc ttcaaccctc     240
tgggagagaa aatga                                                       255
```

<210> SEQ ID NO 2
<211> LENGTH: 84
<212> TYPE: PRT
<213> ORGANISM: Homo sapiens

<400> SEQUENCE: 2

```
Met Met Ala Leu Arg Ser Gln Gly Leu Met Leu Pro Gln Ser Cys Pro
1               5                   10                  15

Gln Leu Ala Phe Leu Thr Leu Ser Ala Leu Ala Ala Val Ser Phe Ser
            20                  25                  30

Ala Leu His Leu Trp Leu Ser Gly Glu Pro Val Gln Ser Ser Gly Thr
        35                  40                  45

Lys Asp Met Arg Ser Lys Ser Asp Ser Lys Arg Val Ser Asp Lys Gln
    50                  55                  60

Leu Ile Ser Lys Ala Val Trp Trp Thr Phe Phe Leu Pro Ser Thr Leu
```

```
                65                  70                  75                  80

Trp Glu Arg Lys

<210> SEQ ID NO 3
<211> LENGTH: 153
<212> TYPE: DNA
<213> ORGANISM: Homo sapiens

<400> SEQUENCE: 3
catctctggc ttagtgggga gccagtccag agctctggaa caaaggacat gagatccaaa      60
tccgattcca agcgagtgag tgacaagcag ctaatttcca aagctgtgtg gtggacattt     120
tttcttcctt caaccctctg ggagagaaaa tga                                  153

<210> SEQ ID NO 4
<211> LENGTH: 51
<212> TYPE: PRT
<213> ORGANISM: Homo sapiens

<400> SEQUENCE: 4

Leu His Leu Trp Leu Ser Gly Glu Pro Val Gln Ser Ser Gly Thr Lys
1               5                   10                  15

Asp Met Arg Ser Lys Ser Asp Ser Lys Arg Val Ser Asp Lys Gln Leu
            20                  25                  30

Ile Ser Lys Ala Val Trp Trp Thr Phe Phe Leu Pro Ser Thr Leu Trp
        35                  40                  45

Glu Arg Lys
    50

<210> SEQ ID NO 5
<211> LENGTH: 13
<212> TYPE: PRT
<213> ORGANISM: Homo sapiens

<400> SEQUENCE: 5

Trp Thr Phe Phe Leu Pro Ser Thr Leu Trp Glu Arg Lys
1               5                   10

<210> SEQ ID NO 6
<211> LENGTH: 23
<212> TYPE: PRT
<213> ORGANISM: Homo sapiens

<400> SEQUENCE: 6

Ser Gly Glu Pro Val Gln Ser Ser Gly Thr Lys Asp Met Arg Ser Lys
1               5                   10                  15

Ser Asp Ser Lys Arg Val Ser
            20

<210> SEQ ID NO 7
<211> LENGTH: 23
<212> TYPE: PRT
<213> ORGANISM: Homo sapiens

<400> SEQUENCE: 7

Asp Lys Gln Leu Ile Ser Lys Ala Val Trp Trp Thr Phe Phe Leu Pro
1               5                   10                  15

Ser Thr Leu Trp Glu Arg Lys
            20

<210> SEQ ID NO 8
<211> LENGTH: 8
```

```
<212> TYPE: PRT
<213> ORGANISM: Homo sapiens

<400> SEQUENCE: 8

Pro Ser Thr Leu Trp Glu Arg Lys
1               5

<210> SEQ ID NO 9
<211> LENGTH: 13
<212> TYPE: PRT
<213> ORGANISM: Homo sapiens

<400> SEQUENCE: 9

Ala Val Trp Trp Thr Phe Phe Leu Pro Ser Thr Leu Trp
1               5                   10

<210> SEQ ID NO 10
<211> LENGTH: 16
<212> TYPE: PRT
<213> ORGANISM: Homo sapiens

<400> SEQUENCE: 10

Lys Arg Glu Trp Leu Thr Ser Pro Leu Phe Phe Thr Trp Trp Val Ala
1               5                   10                  15

<210> SEQ ID NO 11
<211> LENGTH: 5
<212> TYPE: PRT
<213> ORGANISM: Homo sapiens

<400> SEQUENCE: 11

Trp Thr Phe Phe Leu
1               5

<210> SEQ ID NO 12
<211> LENGTH: 24
<212> TYPE: PRT
<213> ORGANISM: Homo sapiens

<400> SEQUENCE: 12

Ser Lys Arg Val Ser Asp Lys Gln Leu Ile Ser Lys Ala Val Trp Trp
1               5                   10                  15

Thr Phe Phe Leu Pro Ser Thr Leu
            20

<210> SEQ ID NO 13
<211> LENGTH: 24
<212> TYPE: PRT
<213> ORGANISM: Canis sp.

<400> SEQUENCE: 13

Ser Lys Gln Val Ser Asp Lys Gln Leu Ile Ser Lys Ala Val Gln Arg
1               5                   10                  15

Ile Phe Phe Phe Leu Gln Pro Ser
            20

<210> SEQ ID NO 14
<211> LENGTH: 24
<212> TYPE: PRT
<213> ORGANISM: Rattus sp.

<400> SEQUENCE: 14

Ser Lys Phe Met Ser Asp Lys Gln Leu Ile Ser Lys Ala Val Gln Arg
1               5                   10                  15
```

Ile Phe Phe Leu Ser Ser Thr Leu
            20

<210> SEQ ID NO 15
<211> LENGTH: 24
<212> TYPE: PRT
<213> ORGANISM: Artificial Sequence
<220> FEATURE:
<223> OTHER INFORMATION: Consensus peptide of sequences from human, dog
      and rat thymus
<220> FEATURE:
<221> NAME/KEY: MISC_FEATURE
<222> LOCATION: (3)..(3)
<223> OTHER INFORMATION: X represents R, Q, F, H, K, N, D, E, Y or W
<220> FEATURE:
<221> NAME/KEY: MISC_FEATURE
<222> LOCATION: (4)..(4)
<223> OTHER INFORMATION: X represents V, M, I or L
<220> FEATURE:
<221> NAME/KEY: MISC_FEATURE
<222> LOCATION: (15)..(15)
<223> OTHER INFORMATION: X represents W, Q, F, Y, N, D or E
<220> FEATURE:
<221> NAME/KEY: MISC_FEATURE
<222> LOCATION: (16)..(16)
<223> OTHER INFORMATION: X represents W, R, F, Y, H or K
<220> FEATURE:
<221> NAME/KEY: MISC_FEATURE
<222> LOCATION: (17)..(17)
<223> OTHER INFORMATION: X represents T, I, S, P, A, G, L, V or M
<220> FEATURE:
<221> NAME/KEY: MISC_FEATURE
<222> LOCATION: (21)..(21)
<223> OTHER INFORMATION: X represents P, L, S, T, A, G, I, V or M

<400> SEQUENCE: 15

Ser Lys Xaa Xaa Ser Asp Lys Gln Leu Ile Ser Lys Ala Val Xaa Xaa
1               5                   10                  15

Xaa Phe Phe Leu Xaa Ser Thr Leu
            20

<210> SEQ ID NO 16
<211> LENGTH: 21
<212> TYPE: PRT
<213> ORGANISM: Artificial Sequence
<220> FEATURE:
<223> OTHER INFORMATION: Consensus peptide of sequences from human, dog
      and rat thymus
<220> FEATURE:
<221> NAME/KEY: MISC_FEATURE
<222> LOCATION: (3)..(3)
<223> OTHER INFORMATION: X represents R, Q, F, H, K, N, D, E, Y or W
<220> FEATURE:
<221> NAME/KEY: MISC_FEATURE
<222> LOCATION: (4)..(4)
<223> OTHER INFORMATION: X represents V, M, I or L
<220> FEATURE:
<221> NAME/KEY: MISC_FEATURE
<222> LOCATION: (15)..(15)
<223> OTHER INFORMATION: X represents W, Q, F, Y, N, D or E
<220> FEATURE:
<221> NAME/KEY: MISC_FEATURE
<222> LOCATION: (16)..(16)
<223> OTHER INFORMATION: X represents W, R, F, Y, H or K
<220> FEATURE:
<221> NAME/KEY: MISC_FEATURE
<222> LOCATION: (17)..(17)
<223> OTHER INFORMATION: X represents T, I, S, P, A, G, L, V or M
<220> FEATURE:
<221> NAME/KEY: MISC_FEATURE
<222> LOCATION: (21)..(21)
<223> OTHER INFORMATION: X represents P, L, S, T, A, G, I, V or M

<400> SEQUENCE: 16

Ser Lys Xaa Xaa Ser Asp Lys Gln Leu Ile Ser Lys Ala Val Xaa Xaa

```
1               5                  10                 15

Xaa Phe Phe Leu Xaa
            20

<210> SEQ ID NO 17
<211> LENGTH: 19
<212> TYPE: PRT
<213> ORGANISM: Artificial Sequence
<220> FEATURE:
<223> OTHER INFORMATION: Consensus peptide of sequences from human, dog
      and rat thymus
<220> FEATURE:
<221> NAME/KEY: MISC_FEATURE
<222> LOCATION: (3)..(3)
<223> OTHER INFORMATION: X represents R, Q, F, H, K, N, D, E, Y or W
<220> FEATURE:
<221> NAME/KEY: MISC_FEATURE
<222> LOCATION: (4)..(4)
<223> OTHER INFORMATION: X represents V, M, I or L

<400> SEQUENCE: 17

Ser Lys Xaa Xaa Ser Asp Lys Gln Leu Ile Ser Lys Ala Val Gln Arg
1               5                  10                 15

Ile Phe Phe

<210> SEQ ID NO 18
<211> LENGTH: 24
<212> TYPE: PRT
<213> ORGANISM: Artificial Sequence
<220> FEATURE:
<223> OTHER INFORMATION: Consensus peptide of sequences from human, dog
      and rat thymus
<220> FEATURE:
<221> NAME/KEY: MISC_FEATURE
<222> LOCATION: (3)..(3)
<223> OTHER INFORMATION: X represents R, Q, F, H, K, N, D, E, Y or W
<220> FEATURE:
<221> NAME/KEY: MISC_FEATURE
<222> LOCATION: (4)..(4)
<223> OTHER INFORMATION: X represents V, M, I or L
<220> FEATURE:
<221> NAME/KEY: MISC_FEATURE
<222> LOCATION: (21)..(21)
<223> OTHER INFORMATION: X represents P, L , S, T, A, G, I, V or M

<400> SEQUENCE: 18

Ser Lys Xaa Xaa Ser Asp Lys Gln Leu Ile Ser Lys Ala Val Gln Arg
1               5                  10                 15

Ile Phe Phe Leu Xaa Ser Thr Leu
            20

<210> SEQ ID NO 19
<211> LENGTH: 20
<212> TYPE: DNA
<213> ORGANISM: Artificial Sequence
<220> FEATURE:
<223> OTHER INFORMATION: Oligonucleotide

<400> SEQUENCE: 19
atggcactca gaagccaggg                                           20

<210> SEQ ID NO 20
<211> LENGTH: 20
<212> TYPE: DNA
<213> ORGANISM: Artificial Sequence
```

```
<220> FEATURE:
<223> OTHER INFORMATION: Oligonucleotide

<400> SEQUENCE: 20
cactcgcttg gaatcggatt                                              20
```

THYMUS-SPECIFIC PROTEIN

CROSS-REFERENCE

This is a National Phase Application filed under 35 U.S.C. 371 of International Application No. PCT/IL2005/001113, filed Oct. 26, 2005, claiming the benefit under 35 USC 119(e) of U.S. Provisional Application No. 60/621,086, filed Oct. 25, 2004, the entire contents of each of which is hereby incorporated herein by reference in its entirety.

FIELD OF THE INVENTION

This invention relates to a novel thymus-specific protein.

PRIOR ART

The following prior publications are considered to be relevant in illustrating the background art to the present invention:

[1] Maurer, H R, Eckert, K, Stange, R: Einfluss der Therapie mit Thymoject auf die antitumorale Immunotoxizität der Leukozytern von Mamma-Tumorpatientinnen. Pers. Mitt. (1999).

[2] Mustacchi, G, Paves, L, Milani, S et al. High-dose folinic acid and fluouracil plus or minus thymostimulin for the treatment of metastatic colorectal cancer: results of a randomised multicentered trial. Anticancer Res. (1994) 14:617-619.

[3] Schulof, R S, Loyd, M J, Cleary, P A, et al. A randomized trial to evaluate the immunorestorative properties of synthetic thymosin-alpha1 in patients with lung cancer. J Biol Resp Modif (1985) 4: 147-158.

[4] Azizi A, Brenner H J, Shoham J: Postoperative adjuvante Behandlung von Patienten mit malignem Melanom durch den Thymusfaktor Thymostimulin. Arzneim-Forsch/Drg Res (1984) 34(II): 1043-1046.

[5] Massimo F, Gobbi P, Moretti G, Avanzini P, Italian Lymphoma Study Group: Effects of Thymostimulin with combination Chemotherapy in patients with aggressive non-Hogkins lymphoma. Am J Clin Oncol (CCT) (1995) 18(1): 8-14.

[6] Peretti P, Tonelli F, Mazzei T, Ficari F, Italian study group on antimicrobal prophylaxis in abdominal surgery. J Chemotherapy (1993) 5(1): 37-42.

[7] Gonelli S, Petrioli R, Cepollaro C, Palmieri R, Aquino A, Gennari C: Thymostimulin in association with chemotherapy in breast cancer patients with bone metastases. Clin Drug Invest (1995) 9(2): 79-87.

[8] Iaffaioli R V, Frasci G, Tortora G, Ciardiello F, Nuzzo F, Scala S, Pacelli R, Bianco A R: Effect of thymic extract Thymostimulin on the incidence of infections and myelotoxicity during adjuvant chemotherapy for breast cancer. Thymus (1988) 12: 69-75. Kluwer Academic Publishers.

These publications will be referred to in the text below by indicating their number from the above list within brackets.

BACKGROUND OF THE INVENTION

Currently, many biological response modifiers (BRM) have been identified. Examples include interleukins and cytokines. The thymus also plays an important role in the overall immunomodulation. One could say that the thymus is the brain of the immune system. The thymus is considered to have a key function in the development and function of the immune system and the biological defense mechanisms against cancer and chronically infected cells.

Thymic tissue is responsible for selected transformation of precursor cells into different T-cells: i.e., helper (CD4+) T-lymphocytes, which aid in the differentiation of other lymphocytes; killer cells (NK cells); cytotoxic cells; and suppressor (cytotoxic) (CD8+) T-lymphocytes (1-3) Having been released into the bloodstream, intestinal and peripheral tissues, the lymphocytes are characterized by well-defined antigens or activation markers on their surface. Their activities are extra-thymic.

There is a delicate interaction between the thymus and the active bone marrow. There is a direct and positive correlation between hypo-function of the thymus and the decline of production of colony-stimulating factors (CSF). Therefore, in cases where there is insufficient production of CSF, the therapeutic application of thymus peptides can be helpful.

Chronic hepatitis B (CHB), HIV, chronic hepatitis C (CHC) and malaria are chronic diseases from which tens of million of people currently suffer without any cure. The cellular branch of immunity is responsible for vigilance against these chronic viruses, fungi, yeast, and parasitic infections as well as against neoplasms and the symptoms of aging. Thymus extracts have been used clinically in a variety of ways involving some of these conditions. They have been used orally and as injectables, by themselves and in combination with other therapeutics. Thymus extracts have been used to treat severe and chronic allergies involving the respiratory tract and skin as well as in severe acute and chronic infectious diseases. The extracts have also been shown to reduce post-surgical infections and decrease the damage of chemotherapy and radiation, and have also been used as adjuncts to mainstream therapy for treatment of neoplasm. All of these conditions have been treated successfully with thymus extracts from bovine.

In a randomized study in patients with malignant melanoma, thymus peptides caused an increased tumor-free period, a longer survival time and increased quality of life (4). In another randomized study in intermediate- and high-grade non-Hodgkins lymphoma, patients were treated with thymus peptides in addition to standard chemotherapy. The treated patients tolerated thymus peptides quite well and had a significantly higher complete response rate than those patients who did not receive thymus peptides (5). In a further randomized study in patients undergoing colorectal surgery showed that the patients who received thymus peptides in addition to Cefotetan did significantly better in lowering the rate of abdominal abscesses and upper respiratory tract infections (6). A randomized study performed in women with advanced breast cancer documented that the women who received thymus peptides in addition to their chemotherapy regimen tolerated the chemotherapy significantly better and had a reduced rate of secondary infections (7,8).

In line with the above findings, its appears that thymus peptides can be used for enhancing bone marrow function and protecting the patient against myelo-suppression of standard chemotherapy; for supporting bone marrow recovery after radiation and chemotherapy; for preventing secondary infections due to immunosuppression caused by standard chemotherapy and surgical interventions; for increasing the complete and partial response rate to anticancer therapies; and for improving lymphocyte function and biological defense mechanisms.

The immune system is composed of many different cells, including T-cells, B-cells, NK-cells, etc. The origin of these different cells varies. Premature T-cells originate in the bone marrow and later on move to the thymus. Different processes take place in the thymus that lead to the production of mature T-cells and to the secretion of various peptides that control the immune response. The T-cells can be divided into several sub-groups, e.g., T-helper cells, T-cytotoxic cells, T-memory cells and T-regulatory cells. Each subset has its own function during the immune response. These sub-groups are characterized by the different antigens presented on their membranes. For example, T-helper cells present the CD4 antigen on their membrane, while T-cytotoxic cells present the CD8 antigen on their membrane.

CD4+ T-cell play a regulatory and are believed to be linked to peripheral self tolerance. The existence of thymus-derived regulatory T-cells was initially suggested by the onset of autoimmune diseases in mice after thymectomy on day 3 of life. These disorders were found to be due to loss of peripheral CD4+ T-cells that constitutively express IL-2R alpha (CD25), which appears late in the periphery after birth. Physiologically generated CD4+CD25+cells inhibit a wide range of autoimmune and inflammatory disorders, e.g. colitis.

Despite numerous studies, the mechanism by which CD4+ CD25+ T-cells exert their regulatory function is unclear. Some studies have shown that regulation in vivo is dependent on the production of suppressive cytokines such as IL-10 and TGF-β and cell-surface molecules such as CTLA-4. In vivo studies have shown that the suppressive effect is not mediated by cytokiaes but rather by cell contact.

CD8+ T-cells have been reported to be essential in vivo to prevent experimental autoimmune encephalomyelitis and to participate in oral tolerance. Regulatory CD8+CD28-T-cells can be generated and expanded in vitro by multiple rounds of stimulations by allogenic APC's but it is not known whether this population exists in vivo. A new study revealed a new regulatory population of CD8+ cells which also constitutively expresses CD25 and which possesses very similar characteristics to CD4+CD25+ cells.

These cells produced IL-10, Foxp3, and CTLA-4 and inhibit CD25-T-cell response to anti-CD3 stimulation through cell contacts with efficiency similar to CD4+CD25+.

It is believed that these 2 subpopulations of cells, CD4+ CD25+ and CD8+CD25+, participate in the regulation of the irnmune response.

SUMMARY OF THE INVENTION

It is an object of the invention to provide a tissue-specific protein from the human thymus.

Using PCR, human cDNA libraries of a 20-year-old woman from 16 different tissues were screened and a cDNA unique for the human thymus was identified. The peptide encoded by the cDNA has been named T101. The human, mouse and rat EST banks were screened and no similarity of the cDNA of T101 to any known gene was found. Similar results were obtained with protein and total genomic DNA banks. The CDNA and the corresponding amino acid sequence are novel sequences, not previously described.

The peptide encoded by the cDNA is 84 amino acids long and includes a signal peptide of 33 amino acids on its N-terminal end (see FIG. 1). The cDNA sequence (SEQ. ID. NO: 1) and amino acid sequence (SEQ. ID. NO: 2) of T101 are as follows:

```
                                           (SEQ. ID. NO: 1)
atgatggcactcagaagccaggggctatgttaccccagagctgcccacaa ctggctttcctcaccctaagtgccttggcagcagtgtcttttcagctct gcatctctggcttagtggggagccagtccagagctctggaacaaaggaca
```

-continued
```
tgagatccaaatccgattccaagcgagtgagtgacagcagctaatttcca aagctgtgtggtggacattttttcttccttcaaccctctgggagagaaaa tga
```

(SEQ. ID. NO: 2)
MMALRSQGLMLPQSCPQLAFLTLSALAAVSFSALHLWLSGEPVQSSGTKD
MRSKSDSKRVSDKQLISKAVWWTFFLPSTLWERK

Provided by the present invention are thus a nucleic acid molecule of SEQ. ID. NO: 1 and a peptide of SEQ. ID. NO: 2. A polypeptide of SEQ. ID. NO: 2 will be referred to herein as the "full T101 peptide".

The full T101 peptide also includes a 33-amino acid signal sequence. Thus, the invention also provides a peptide comprising the sequence of the full T101 peptide, without said signal peptide, consisting of the following sequence (SEQ ID. NO: 4):

(SEQ. ID. NO: 4)
LHLWLSGEPVQSSGTKDMRSKSDSKRVSDKQLISKAVWWTFFLPSTLWE
RK

The T101 peptide that is devoid of the signal sequence (SEQ. ID. NO: 4) will be referred to herein as the "T101 peptide".

Also provided by the invention is a nucleic acid molecule comprising a sequence encoding for the T101 peptide. This includes the following sequence (SEQ. ID. NO: 3):

```
                                           (SEQ. ID. NO: 3)
catctctggcttagtggggagccagtccagagctctggaacaaag gacatgagatccaaatccgattccaagcgagtgagtgacaagcag ctaatttccaaagctgtgtggtggacattttttcttccttcaacc ctctgggagagaaaatga
```

The invention also provides modified nucleic acid molecules of SEQ. ID. NO: 1 or SEQ. ID. NO: 3 and modified peptides of SEQ. ID. NO: 2 or SEQ. ID. NO: 4, in which one or more nucleotides or amino acid residues, respectively, is added, deleted or replaced, without significantly affecting the biological characteristics of the modified molecule as compared to the unmodified molecule.

The term "peptide" is used herein to denote a peptide, polypeptide or protein. The peptide may be obtained synthetically, through genetic engineering methods, expression in a host cell, or through any otlher suitable means.

The term "biological characteristics", with respect to a peptide molecule, refers to the peptide's ability to exert at least one of the in vitro or in vivo effects that may be exerted by the full T101 peptide or the T101 peptide, including but not limited to the biological activities reported below in the Examples. The term "biological characteristics", with respect to a nucleic acid molecule, refers to the property of encoding a peptide having similar biological characteristics to that of the full T101 peptide or the T101 peptide, including, in particular: (i) a nucleic acid molecule that has a different sequence to that of SEQ. ID. NO: 1 or SEQ. ID. NO: 3, but, owing to the redundancy of the genetic code, encodes the full T101 peptide or the T101 peptide, respectively; and (ii) a nucleic acid molecule that encodes an amino acid molecule with a different sequence than that of the full T101 peptide or the T101 peptide but that has similar biological characteristics to that of the full T101 peptide or the T101 peptide, respectively.

The term "without significantly affecting the biological characteristics of the modified molecule as compared to the unmodified molecule" means to denote that the modified molecule retains a biological activity qualitatively similar to that of the unmodified molecule. With respect to a modified peptide, this means that it retains one or more of the biological characteristics of a peptide of SEQ. ID. NO: 2 or SEQ. ID. NO: 4, including, among others, its diagnostic and therapeutic utilities, as specified below, as well as its in vitro and in vivo activities reported in the Examples below. In order to determine whether a peptide retains a biological activity qualitatively similar to that of the unmodified molecule, one or more assays can be carried out, such as for example an in vitro, in vivo or a clinical experiment in which a modified peptide is compared to the corresponding unmodified one (namely that of the full T101 peptide or the T101 peptide) that is assayed in parallel; or an experiment in which the rmodified peptide is assayed to examine whether it has a biological effect similar to that of the unmodified peptide as known from separately conducted experiment. Such an experiment may be carried out, for example, in manner described in the Examples below. With respect to a modified nucleic acid molecule, the term "without significantly affecting the biological characteristics of the modified molecule as compared to the unmodified molecule" denotes the property of encoding a modified peptide of any of the above characteristics.

A modified peptide may be a peptide that includes a contiguous sequence of at least 8, 12, 15, 20, 25, 30, 35, 40 or at least 45 amino acid residues that has a degree of identity to a corresponding sequence of at least 8, 12, 15, 20, 25, 30, 35, 40 or at least 45 amino acid residues included in the T101 peptide, the degree of identity being at least 70%, preferably at least 80%, mare preferably at least 90% and particularly at least 95%.

The invention further provides a peptide comprising a partial contiguous sequence from the full T101 peptide including at least 8 amino acid residues, which contiguous sequence is included as a contiguous sequence in said full T101 peptide. Such a peptide will be referred to herein as a "partial T101" peptide. In one embodiment, the invention provides a partial T101 peptide that comprises a contiguous sequence of 13 amino acid residues beginning from the C-terminal end of the T101 peptide (amino acid numbers 39 to 51), as follows:

```
       WTFFLPSTLWERK.        (SEQ. ID. NO: 5)
```

The invention further provides a protein or polypeptide comprising an amino acid sequence of the full T101 peptide, T101 peptide, modified peptide or a partial T101 peptide (such protein or polypeptide will be referred to herein as "T101 comprising protein"). The T101 comprising protein may, for example, be a fusion protein that comprises the full T101 peptide, the T101 peptide, a modified peptide or a partial T101 peptide; it may be a conjugate of a protein or another peptide or polypeptide with the full T101 peptide, T101 peptide, modified peptide or partial T101 peptide; etc.

The invention also provides an oligonucleotide of at least 24 nucleotides that is: (i) an oligonucleotide that encodes a partial contiguous sequence from the T101 peptide including at least 8 amino acid residues, which may include a contiguous 24 nucleic acid sequence included in SEQ. ID. NO: 1; (ii) a nucleotide sequence that can hybridize to a nucleotide sequence of SEQ. ID. NO: 1 under stringent hybridization conditions; (iii) an oligoinucleotide that has a sequence of at least 24 contiguous nucleotides with a degree of identity to a corresponding contiguous sequence of nucleotides included in SEQ. ID. NO: 1 of at least 70%, preferably at least 80%, more preferably at least 90% and particularly at least 95%.

The invention also provides a nucleic acid molecule, e.g. a transfer vector or an expression vector, comprising any of the aforementioned nucleic acid molecules.

In another aspect of the invention, there are provided additional partial T101 peptides as follows:

```
SGEPVQSSGTKDMRSKSDSKRVS    (SEQ. ID. NO:  6)

DKQLISKAVWWTFFLPSTLWERK    (SEQ. ID. NO:  7)

PSTLWERK                   (SEQ. ID. NO:  8)

AVWWTFFLPSTLW              (SEQ. ID. NO:  9)

KREWLTSPLFFTWWVA           (SEQ. ID. NO: 10)

WTFFL                      (SEQ. ID. NO: 11)
```

SEQ. ID. NO: 6 consists of amino acids 6 to 28 of the T101 peptide; SEQ. ID. NO: 7 consists of amino acids 29 to 51 of the T101 peptide; SEQ. ID. NO: 8 consists of amino acids 44 to 51 of the T101 peptide; SEQ. ID. NO: 9 consists of amino acids 36 to 48 of the T101 peptide; SEQ. ID. NO: 10 consists of amino acids 36 to 51 of the T101 peptide in the reverse order; SEQ. ID. NO: 11 consists of amino acids 39 to 43 of the T101 peptide.

Also provided by the invention are modified peptides derived from any of the peptides defined above, e.g., modified peptides in which one or more amino acids are replaced by another amino acid by conservative substitution. As used herein, "conservative substitution" refers to the substitution of an amino acid in one class by an amino acid of the same class, where a class is defined by common physicochemical amino acid side chain properties and high substitution frequencies in homologous proteins found in nature. Six general classes of amino acid side chains have been categorized and include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu is a conservative substitution.

In one embodiment, only one substitution is made in the amino acid sequence. In another embodiment, two substitutions are made. In a further embodiment, three substitutions are made. The maximum number of substitutions should not exceed that number of amino acids which leaves at least 70%, desirably at least 80%, preferably at least 90%, most preferably at least 95% of the amino acids in the unsubstitued sequence. By 4one preferred embodiment, the substitutions which include up to 3, at times up to 6 amino acid residues substituted by others, are conservative substitutions.

In a further embodiment, one or more arnino acids may be replaced by D-amino acids, preferably the corresponding D-amino acids.

In a still further embodiment, sequences of the reverse order of the above sequences are also included in the invention.

Thus, also provided by the invention are full T101 peptides of SEQ ID NO: 2 or preferably T101 peptides of SEQ ID NO: 4 or partial T101 sequences thereof, modified by one or more conservative substitutions.

Provided is thus a peptide including at least 10, or 15, or 20, or 25, or 30, or 35, or 40 amino acid residues or the entire sequence of the T101 peptide having the sequence: $AA_1$-$AA_2$-....-$AA_{51}$, wherein:

$AA_1$ is selected from leucine, isoleucine, valine and methionine;
$AA_2$ is selected from lysine, arginine and histidine;
$AA_3$ is selected from leucine, isoleucine, valine and methionine;
$AA_4$ is selected from tryptophan, phenylalanine and tyrosine;
$AA_5$ is selected from leucine, isoleucine, valine and methionine;
$AA_6$ is selected from serine, threonine, alanine, glycine and proline;
$AA_7$ is selected from serine, threonine, alanine, glycine and proline;
$AA_8$ is selected from glutamine, glutamic acid, aspartic acid and asparagine;
$AA_9$ is selected from serine, threonine, alanine, glycine and proline;
$AA_{10}$ is selected from leucine, isoleucine, valine and methionine;
$AA_{11}$ is selected from glutamine, glutamic acid, aspartic acid and asparagine;
$AA_{12}$ is selected from serine, threonine, alanine, glycine and proline;
$AA_{13}$ is selected from serine, threonine, alanine, glycine and proline;
$AA_{14}$ is selected from serine, threonine, alanine, glycine and proline;
$AA_{15}$ is selected from serine, threonine, alanine, glycine and proline;
$AA_{16}$ is selected from lysine, arginine and histidine;
$AA_{17}$ is selected from glutamine, glutamic acid, aspartic acid and asparagine;
$AA_{18}$ is selected from leucine, isoleucine, valine and methionine;
$AA_{19}$ is selected from lysine, arginine and histidine;
$AA_{20}$ is selected from serine, threonine, alanine, glycine and proline;
$AA_{21}$ is selected from lysine, arginine and histidine;
$AA_{22}$ is selected from serine, threonine, alanine, glycine and proline;
$AA_{23}$ is selected from glutamine, glutamic acid, aspartic acid and asparagine;
$AA_{24}$ is selected from serine, threonine, alanine, glycine and proline;
$AA_{25}$ is selected from lysine, arginine and histidine;
$AA_{26}$ is selected from lysine, arginine and histidine;
$AA_{27}$ is selected from leucine, isoleucine, valine and methionine;
$AA_{28}$ is selected from serine, threonine, alanine, glycine and proline;
$AA_{29}$ is selected from glutamine, glutamic acid, aspartic acid and asparagine;
$AA_{30}$ is selected from lysine, arginine and histidine;
$AA_{31}$ is selected from glutamine, glutamic acid, aspartic acid and asparagine;
$AA_{32}$ is selected from leucine, isoleucine, valine and methionine;
$AA_{33}$ is selected from leucine, isoleucine, valirne and methionine;
$AA_{34}$ is selected from serine, threonine, alanine, glycine and proline;
$AA_{35}$ is selected from lysine, arginine and histidine;
$AA_{36}$ is selected from serine, threonine, alanine, glycine and proline;
$AA_{37}$ is selected from leucine, isoleucine, valine and methionine;
$AA_{38}$ is selected from tryptophan, phenylalanine and tyrosine;
$AA_{39}$ is selected from tryptophan, phenylalanine and tyrosine;
$AA_{40}$ is selected from serine, threonine, alanine, glycine and proline;
$AA_{41}$ is selected from tryptophan, phenylalanine and tyrosine;
$AA_{42}$ is selected from tryptophan, phenylalanine and tyrosine;
$AA_{43}$ is selected from leucine, isoleucine, valine and methionine;
$AA_{44}$ is selected from serine, threonine, alanine, glycine and proline;
$AA_{45}$ is selected from serine, threonine, alanine, glycine and proline;
$AA_{46}$ is selected from serine, threonine, alanine, glycine and proline;
$AA_{47}$ is selected from leucine, isoleucine, valine and methionine;
$AA_{48}$ is selected from tryptophan, phenylalanine and tyrosine;
$AA_{49}$ is selected from glutamine, glutamic acid, aspartic acid and asparagine;
$AA_{50}$ is selected from lysine, arginine and histidine; and
$AA_{51}$ is selected from lysine, arginine and histidine.

Provided are also modified peptides based on the full T101 peptide, T101 peptide or partial T101 peptide, including the following subsequences (amino acid numbering based on the T101 peptide):

$AA_{38}$-$AA_{39}$-$AA_{40}$-$AA_{41}$-$AA_{42}$; wherein $AA_{38}$ and $AA_{39}$ are Class VI amino acids, preferably tryptophan; $AA_{40}$ is a Class II amino acid, preferably threonine; and $AA_{41}$ and $AA_{42}$ are Class VI amino acids, preferably phenylalanine.

$AA_{38}$-$AA_{39}$-$AA_{40}$-$AA_{41}$-$AA_{42}$-$AA_{43}$; wherein $AA_{38}$ and $AA_{39}$ are Class VI amino acids, preferably tryptophan; $AA_{40}$ is a Class II amino acid, preferably threonine; $AA_{41}$ and $AA_{42}$ are Class VI amino acids, preferably phenylalanine; and $AA_{43}$ is a Class V amino acid, preferably leucine.

Ala-Val-$AA_{38}$-$AA_{39}$-$AA_{40}$-$AA_{41}$-$AA_{42}$; wherein $AA_{38}$ and $AA_{39}$ are Class VI amino acids, preferably tryptophan; $AA_{40}$ is a Class II amino acid, preferably threonine; and $AA_{41}$ and $AA_{42}$ are Class VI amino acids, preferably phenylalanine.

Ala-Val-$AA_{38}$-$AA_{39}$-$AA_{40}$-$AA_{41}$,-$AA_{42}$-$AA_{43}$; wherein $AA_{38}$ and $AA_{39}$ are Class VI amino acids, preferably tryptophan; $AA_{40}$ is a Class II amino acid, preferably threonine; $AA_{41}$ and $AA_{42}$ are Class VI amino acids, preferably phenylalanine; and $AA_{43}$ is a Class V amino acid, preferably leucine.

The 24-amino acid sub-sequence of SEQ ID NO: 4 (amino acid nos. 24 to 47):

```
SKRVSDKQLISKAVWWTFFLPSTL,    (SEQ ID NO: 12)
``` corresponds closely to the following sequences from other mammalian species:

```
Dog:
SKQVSDKQLISKAVQRIFFFLQPS;    (SEQ ID NO: 13)
and

Rat:
SKFMSDKQLISKAVQRIFFLSSTL.    (SEQ ID NO: 14)
```

When SEQ ID NOs: 12 through 14 are compared, the following consensus sequence for the three species emerges (shown in capital letters):

```
SKrvSDKQLISKAVwwtFFLpSTL        (SEQ ID NO: 12)

SKqvSDKQLISKAVQRIFFflqps        (SEQ ID NO: 13)

SKfmSDKQLISKAVQRIFFLsSTL        (SEQ ID NO: 14)
```

The present invention thus also provides a peptide comprising said consensus sequence. Such a peptide (to be referred to herein as the "consensus peptide") has one of the following formulae:

```
SKx₁x₂SDKQLISKAVx₃x₄x₅FFLx₆STL;   (SEQ ID NO: 15)

SKx₁x₂SDKQLISKAVx₃x₄x₅FFLx₆;      (SEQ ID NO: 16)

SKx₁x₂SDKQLISKAVQRIFF;            (SEQ ID NO: 17)
or
SKx₁x₂SDKQLISKAVQRIFFLx₆STL;      (SEQ ID NO: 18)
``` wherein:

$x_1$ represents K, Q or F, or alternatively as a result of conservative substitution, H, K, N, D, E, Y or W;

$x_2$ represents V or M, or alternatively as a result of conservative substitution, I or L;

$x_3$ represents W or Q, or alternatively as a result of conservative substitution, F, Y, N, D or E;

$x_4$ represents W or R, or alternatively as a result of conservative substitution, F, Y, H or K;

$x_5$ represents T or I, or alternatively as a result of conservative substitution, S, P, A, G, L, V or M; and $x_6$ represents P, L or S, or alternatively as a result of conservative substitution, T, A, G, I, V or M.

Also provided is a protein or polypeptide that comprises an amino acid sequence of said consensus peptide. The invention further provides a nucleotide sequence encoding said consensus peptides or a protein or polypeptide comprising an amino acid sequence of said consensus peptide.

T101 is soluble in an aqueous solution. This factor and the biological characteristics that will be described below, its tissue specificity and the physical characteristics of a peptide hormone, render the T101 peptide, the full T101 peptide, the partial T101 peptide or any modified peptides thereof useful as therapeutic agents for inducing the cellular immune response and for various other clinical conditions, such as HIV infection, hepatitis B, hepatitis C, cancer and malaria.

As will also be shown further below in the Examples, it has been found that the T101 peptide and various modified peptides derived there from are capable of modulating the immune system. This modulation is expressed both by activation of the immune system (as shown, e.g., by an increase in proliferation of peripheral blood lymphocytes (PBL) as well as by suppression of the immune system (as shown, for example, by an increase in IL-10 production and decrease in PBL). Thus, T101 has both immuno-activating activity and immuno-suppressing activity. Without wishing to be bound by theory and limit the scope of the invention thereby, the types of effects of T101 on the immune system may be concentration-dependent.

The invention also includes methods of treatment, methods of diagnosis and pharmaceutical compositions making use of the T101 peptide, full T101 peptide, partial T101 peptide, modified peptide or T101 comprising protein or of any of the nucleic acid molecules mentioned above. Potential diagnostic and therapeutic applications of the T101 peptide include the following:

1. T101 may serve as a diagnostic tcool for lack of immunocompetence after sub-dermal injection of toxins from different organisms.

2. Testing the level of T101 in the blood may serve as an indicator for high or low thymus function and may serve as an indicator for the level of immune system activity.

3. The level of T101 may serve as an indicator of autoimmune diseases.

4. T101 may serve as a stimulator of the immune system. For example, T101 may be used to treat a lack of immunocompetence to bacteria, parasites and viral toxins.

5. T101 may be utilized as a therapeutic tool for decreasing recurrence of infections. For example, in the respiratory tract, T101 should decrease recurrence of infections.

6. T101 may be utilized as a therapeutic tool for decreasing allergic and inflammatory responses. For example, T101 may be used to decrease the occurrence of asthma or symptoms thereof.

7. T101 may be used to treat viral diseases such as tuberculosis, herpes, acute and chronic hepatitis B, acute and chronic hepatitis C, chronic cholestatic hepatitis, cirrhosis, stomatitis.

8. T101 may be used as a therapeutic tool to treat immunodeficiency diseases such as AIDS and combined immunodeficiency.

9. T101 may be used as a therapeutic tool to treat skin diseases such as atopic eczema and psoriasis.

10. T101 may be used to treat several other diseases. For example, T101 may serve as a suppressor of the immune system to treat autoimmune pathologies such as BDI, myasthenia gravis, multiple sclerosis, diabetes type I, rheumatoid arthritis, systematic lupus, scleroderma, chronic autoimmune hemolytic anemia, colitis and Crohn's disease, etc.

11. T101 may serve as a stimulator of the immune system to treat cancer diseases such as lung cancer, carcinoma of the larynx, carcinoma of head and neck and breast, Hodgkin's disease, non-Hodgkin's lymphoma, breast cancer, hepatocellular cancer, melanoma.

12. T101 may be used to decrease the occurrence of infections after surgery and implants. T101 may be used after transplantations in order to inhibit rejection of grafts.

13. T101 may strengthen the immune response of older or younger persons or persons with compromised immune systems.

14. T101 may be used to treat skin infections after burns.

15. T101 may be used as a therapeutic tool to treat male infertility.

16. T101 may improve cardiac activity.

17. T101 may be used in a method for identifying thymus cells. T101 may also serve as a marker of the thymus and its metabolic condition. For example, T101 may be used in ELISA assays or other assays to measure the metabolic condition of the thymus.

18. T101 may serve as a tool to develop a fluorescent dye to specific subpopulations of WBC to separate different WBC subpopulations from different tissues.

19. T101 may serve as a general stimulator or inhibitor of different immune reactions and may also affect directly or indirectly other organs like the heart and lung etc.

20. T101 can modulate neurological functions such as memory, regeneration of the neural system, pain relief, and neuropathologies such as Parkinson and Alzheimer disease.

21. T101 can serve as a probe to identify specific cells from the immune system and use them for cell therapy.

For the above diagnostic and therapeutic applications, the full T101 peptide, a partial T101 peptide or a T101 comprising protein, or a modified peptide thereof may also be used.

BRIEF DESCRIPTION OF THE DRAWINGS

In order to understand the invention and to see how it may be carried out in practice, results of experiments carried out in accordance with the invention will be described, with reference to the accompanying drawing, in which:

FIG. 1 shows the full sequence of the T101 cDNA and the encoded full T101 peptide. The "full" T101 peptide consists of a signal peptide (indicated by regular font letters) and the T101 peptide (indicated by bold font letters). The cDNA encoding the signal peptide is similarly indicated;

EXAMPLES

Example 1

The amino acid and nucleotide sequences of the full T101 peptide are shown in FIG. 1. The amino acid sequence was subjected to analysis by the Phobius signal peptide predictor tool (available at www.phobius.cgb.ki.se) for prediction of the transmembrane topology and the signal peptide sequence.

Phobius predicted the 33-amino acid C-tenninal sequence of the full T101 peptide as being a hydrophobic, transmembrane signal peptide domain. The signal peptide is indicated in FIG. 1 by regular font letters.

Also using conventional bioinformatics tools, it was found that a 24-amino acid sub-sequence of SEQ ID NO: 4,

```
SKRVSDKQLISKAVWWTFFLPSTL,    (SEQ ID NO: 12)
``` corresponds closely to the following sequences from other mammalian species:

```
Dog:
SKQVSDKQLISKAVQRIFFFLQPS;    (SEQ ID NO: 13)
and

Rat:
SKFMSDKQLISKAVQRIFFLSSTL.    (SEQ ID NO: 14)
```

When SEQ ID NOs: 12 through 14 are compared, the following consensus amino acid residues in these peptides emerge (consensus amino acids shown in capital letters):

```
SKrvSDKQLISKAVwwtFFLpSTL    (SEQ ID NO: 12)

SKqvSDKQLISKAVQRIFFflqps    (SEQ ID NO: 13)

SKfmSDKQLISKAVQRIFFLsSTL    (SEQ ID NO: 14)
```

Example 2 cDNA libraries from 16 different tissues were used to screen for T101. The libraries, purchased from Clontech, included Leukocytes, Testis, Colon, Prostate, Small Intestine, Thymus, Ovary, Spleen, Liver, Kidney, Brain, Lung, Pancreas, Skeletal, Placenta, Heart.

The cDNA libraries were screened by PCR using specific oligos for T101. The sequences of the oligos were deduced from the sequence of T101.

In the PCR experiment, 3 microliters from each of the cDNA libraries, 5 microliters of the specific oligos (total), 20 microliters of Readymix Taq polymerase and 17 microliters of DDW, were used.

The following PCR procedure was employed:
1 min at 95° C.
30 cycles of:
    1 min at 95° C.;
    1 min at 52° C.;
    1 min at 72° C.
After finishing the cycles, samples were kept at 72° C. for 10 min.
The sequences of the oligos that were used were:
(i) OLIGO #5—the label is: H10(180)E1P

```
5'-atggcactcagaagccaggg-3'    (SEQ. ID. NO: 19)
```

(ii) OLIGO #6—the label is: H10(180)E1C

```
5'-cactcgcttggaatcggatt-3'    (SEQ. ID. NO: 20)
```

Figure 2:
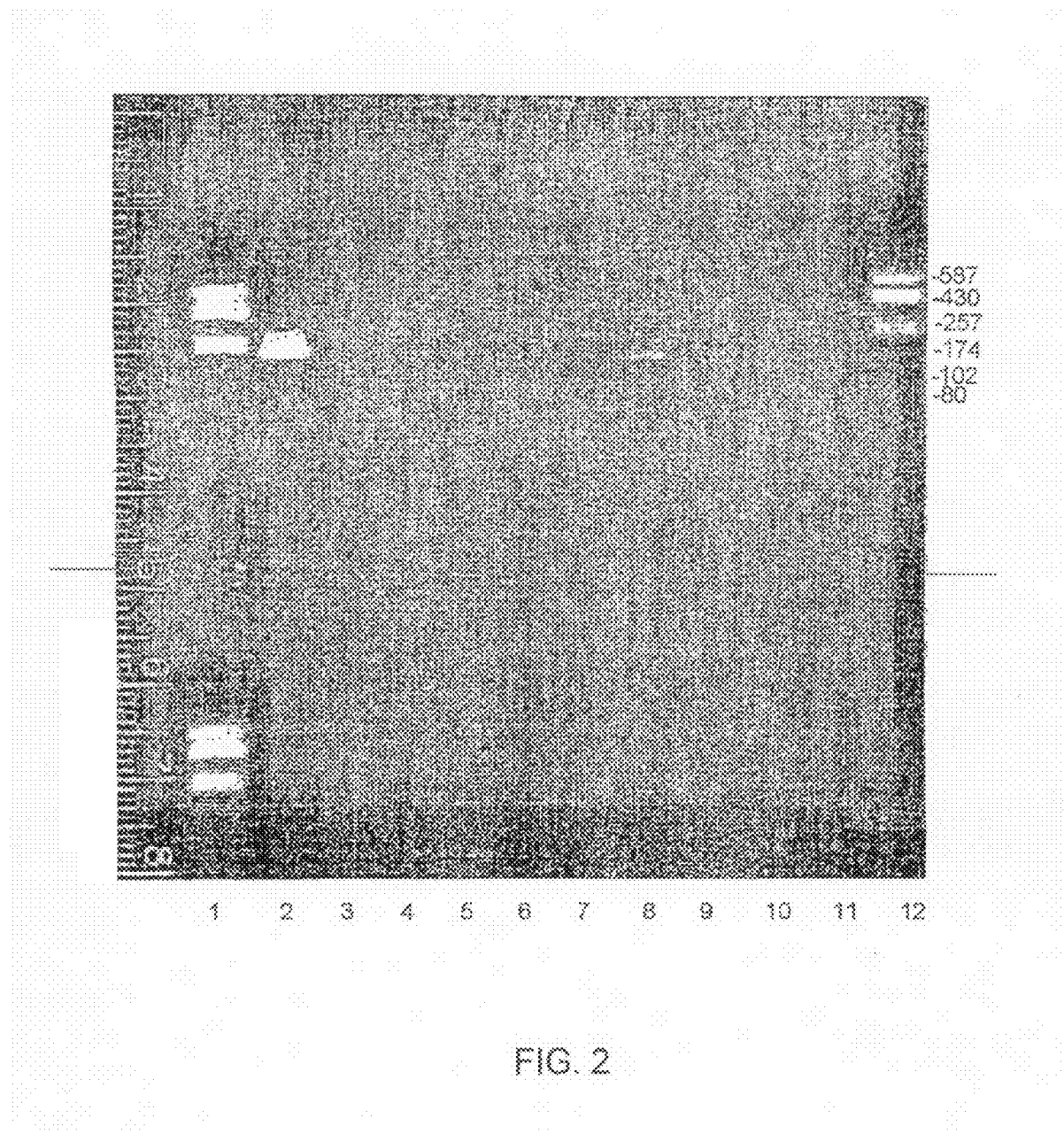
FIG. 2 is a photograph of a PCR gel showing the T101 peptide. The gel contains 12 columns and was run with two arrays of samples: one array beginning at the top of the gel and the other array beginning in the middle of the gel (indicated by the lines on either side of the gel).

The results of the PCR are shown in FIG. 2. The agarose gel shown in FIG. 2 contains 12 columns and was run with two arrays of samples: the first array beginning at the top of the gel and the second array beginning in the middle of the gel (as indicated by the location of the lines on either side of the gel). The samples in the columns in the first array were as follows: 1 & 12. MW markers (molecular weights indicated on right side of gel); 2. growth hormone; 3. Leukocytes; 4. Testis; 5. Colon; 6. Prostate; 7. Small Intestine; 8. Thymus; 9. Ovary; 10. Spleen; 11. Liver. The samples in the columns in the second array are as follows: 1. MW marker; 2. Kidney; 3. Brain; 4. Lung; 5. Pancreas; 6. Skeletal muscle; 7. Placenta; 8. Heart.

It can be seen from the gel that the specific sequence of T101 was found only in the thymus tissue and not in any other tissue tested. The growth hormuone, used here as a positive control, was also found to be positive for T101.

Example 3

The T101 peptide was tested for its ability to activate proliferation of mouse spleenocytes or thymocytes (two mouse strains were used: CD1 and Balb/C), as well as human peripheral blood lymphocytes (PBL). The proliferation activity was measured by 5-bromo 2'-deoxy-uridine (BrdU) incorporation into these cells.

Method

Mouse spleenocytes or thymocytes were isolated from spleen or thymus of Balb/C mice. They were plated in 96-well plates using a concentration (f $10^7$cells/well. RPMI 1640 medium+10% FCS and Pen/Str was used. The cells were treated with different concentrations of the T101 peptide (0.1 or 0.01 μg/well) or with saline (Con), and after 48 hours they were labeled for 6 hours with BrdU and tested for BrdU incorporation into their nucleus.

Human PBL were isolated on a Ficole gradient from blood taken from volunteers and then plated in 96-well plates, again using RPMI 1640+10% FCS+Pen/Str.

The cells were treated with different concentrations of the peptide or saline (as above) and after 48 hours were labeled for 6 hours with BrdU and tested for BrdU incorporation into their nucleus.

Results

Figure 3:
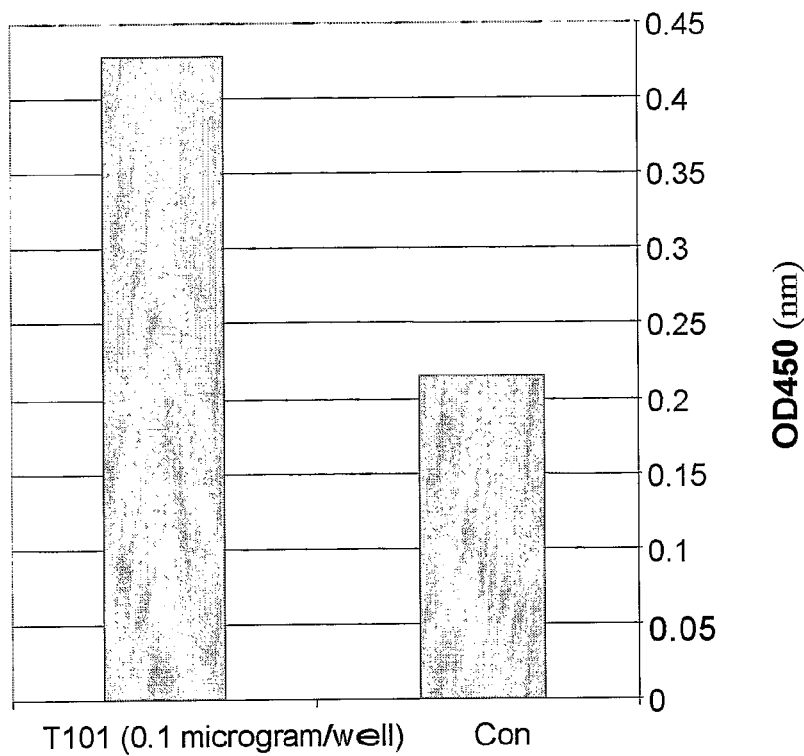
FIG. 3 is a graph showing BrdU incorporation in human PBL incubated with the T101 peptide as compared to control. The Y-axis shows the optical density at 450 nm—a higher OD signifies a higher BrdU incorporation.
Figure 4:
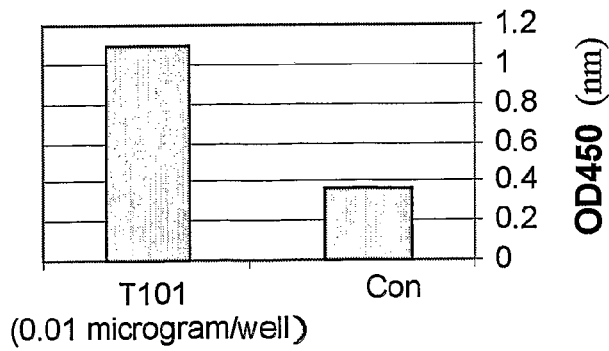
FIG. 4 is a graph showing BrdU incorporation in Balb/c thymocytes incubated with the T101 peptide as compared to control. The Y-axis shows the optical density at 450 nm—a higher OD signifies a higher BrdU incorporation.

As is shown in FIGS. 3 and 4, respectively, in both human PBL and Balb/c thymocytes, T101 was able to increase BrdU incorporation, signifying that T101 was able to induce the cells to increase their proliferation rate.

Example 4

In the next experiment, several deletion mutants of the T101 peptide were constructed and synthesized. These mutants were tested for their ability to stimulate proliferation in human PBL. The right-hand column indicates the fold increase in proliferation over proliferation in untreated cells.

TABLE 1

Stimulation of Proliferation in Human PBL

| Peptide | Amino acid sequence | Fold Increase |
|---|---|---|
| WT | LHLWLSGEPVQSSGTKDMRSKSDSKRV SDKQLISKAVWWTFFLPSTLWERK (SEQ. ID. NO: 4) | 2 |
| Mut #1 | WTFFLPSTLWERK (SEQ. ID. NO: 5) | 2.5-3 |
| Mut #2 | SGEPVQSSGTKDMRSKSDSKRVS (SEQ. ID. NO: 6) | 1.4-1.6 |
| Mut #3 | DKQLISKAVWWTFFLPSTLWERK (SEQ. ID. NO: 7) | 2.2-2.8 |
| Mut #4 | PSTLTWERK (SEQ. ID. NO: 8) | 1.1-1.3 |
| Mut #5 | AVWWTFFLPSTLW (SEQ. ID. NO: 9) | 2-2.2 |
| Mut #6 | KREWLTSPLFFTWWVA (SEQ. ID. NO: 10) | 2-2.4 |

The following conclusions may be reached on the basis of the above results:

1. Mutant #1 consists of the 13 C-terminal amino acids of the T101 peptide, and was very active. It appears that this sequence (or a portion of it) is essential for the proliferation stimulating activity measured.

2. Mutant #2 consists of 23 amino acids upstream to Mutant #1, and had relatively low activity. It appears that this portion of the T101 peptide is less important for this biological activity.

3. Mutant #3 consists of the 23 C-terminal amino acids of the T101 peptide, and in contrast to Mutant #2, was very active. It can thus be seen that some portions of the T101 peptide are more important than others with respect to the stimulating activity.

4. Mutant #4 consists of the 8 C-terminal amino acids of the T101 peptide, and had almost no activity. This indicates that the five N-terminal amino acids of Mutant #1 are crucial for its activity.

5. Mutant #5 consists of 13 amino acids which partially overlap those of Mutant #1. It had a similar activity to the T101 peptide, but less that the activity of Mutant #1.

6. Mutant #6 consists of the amino acid sequence of Mutant #5 in reverse order. It surprisingly had similar activity to that of Mutant #5.

It can thus be seen that not all of the T101 amino acid sequence is required for proliferation stimulating activity.

Example 5

Biotinilated-T101 peptide was synthesized and its binding to human PBLs was determined using a fluorescence microscope.

Method

Biotinilated-T101 peptide in different concentrations was added to $10^6$ cells/tube (human PBLs). A control was also prepared without T101 peptide. In the next step, saturating concentrations of fluorescent anti-biotin antibody were added and the cells were washed 3 times with PBS. The cells were then observed under a fluorescence microscope.

Results

Figure 5:
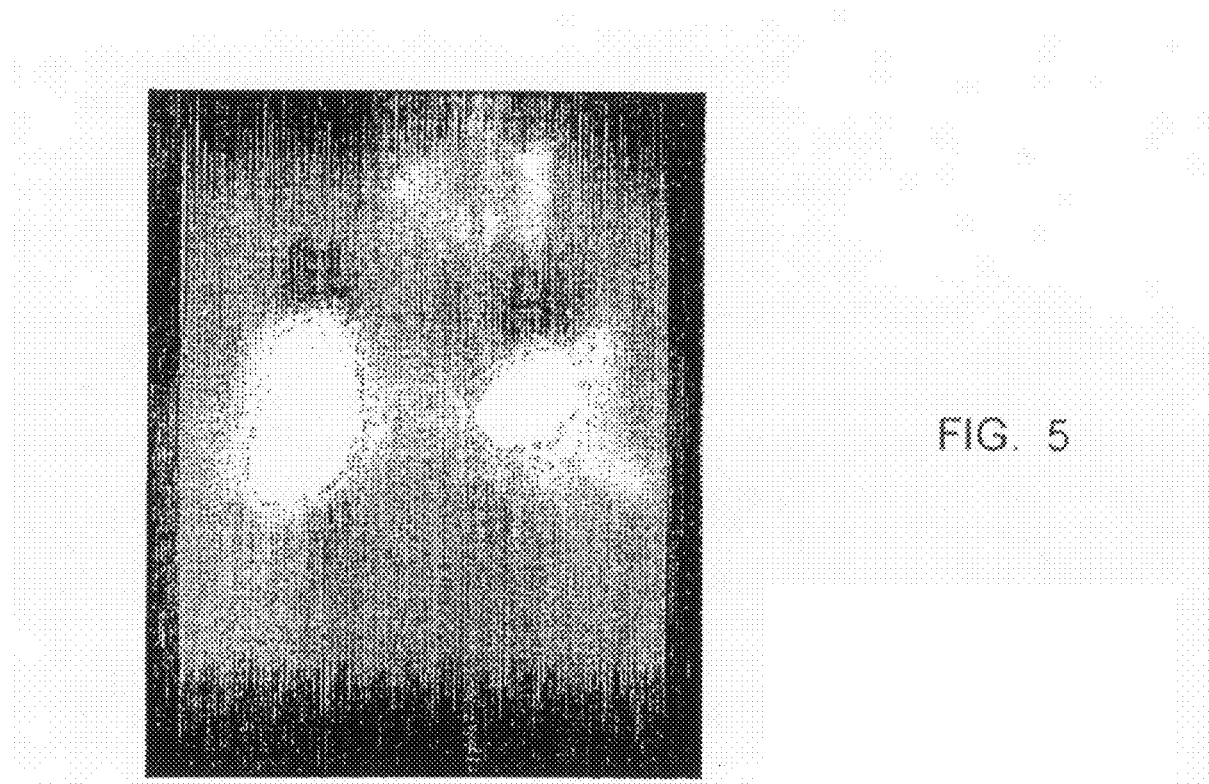
FIG. 5 is a fluorescence micrograph of lymphocytes following incubation with biotinilated T101 peptide.

The results, shown in FIG. 5, indicate that the anti-biotin antibody bound to the cells treated with biotinilated T101. It was found that increasing concentrations of biotinilated-T101 peptide caused an increase in fluorescence (results from FACS not shown). When the biotinilated-T101 peptide is first bound to the antibody and then the conjugate is incubated with the cells, no fluorescence was detected. The control cells had no fluorescence (results not shown in Figure).

In most cases the cells labeled with the biotinilated-T101 peptide were seen clumped together.

This experiment provides direct evidence that T101 can bind to human PBL. Since the antibody cannot penetrate into the cells, and cells not labeled with T101 were not labeled with the anti-biotin antibody, the conclusion is that only cells that externally bound T101 were labeled.

Similar results were obtained with mouse splenocytes.

Example 6

In order to find which subpopulation of lymphocytes binds the T101 peptide, a FACS analysis using mouse spleen or thymus cells was performed. For the analysis several antibodies were used: (1) anti-mouse CD3, (2) anti-mouse CD4, (3) anti-mouse CD8 and (4) anti-mouse CD25.

Method $10^6$ splenocytes were labeled with the biotinilated T101 peptide and PE-streptavidin and an FITC-anti-mouse CD25. For each antibody, its isotype antibody was used as a control.

Results

Figure 6:
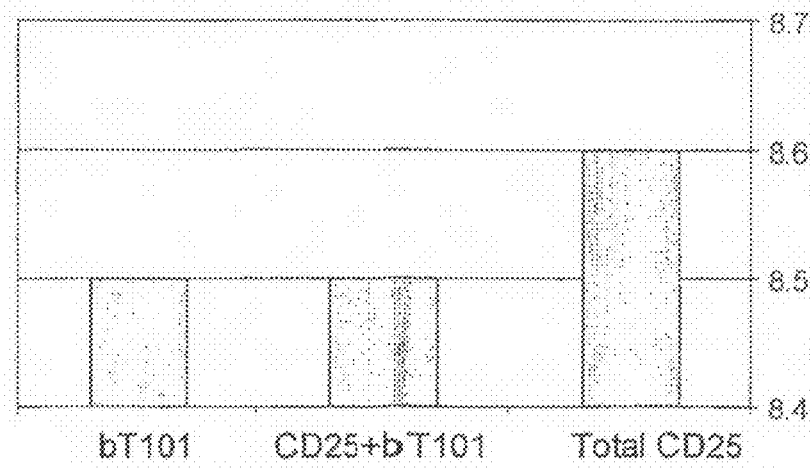
FIG. 6 is a bar graph showing results of an experiment involving labeling by bT101 and/or CD25 of mouse splenocytes through the CD25 antigen. The Y axis shows the % of labeled cells.

Results from a FACS analysis are presented in FIG. 6 (Y axis shows the percentage of labeled cells). The following conclusions may be reached:

(1) Adding the biotinilated T101 peptide caused the appearance of large fluorescent cells, while in the control experiment no such cells were detected (results not shown).
(2) All of the CD25+ cells were also labeled with the biotinilated peptide.
(3) Part of the CD3+, CD4+ and CD8+ cells were labeled with the biotinilated peptide (results not shown).

T101 binds to CD25+ cells, CD4+ cells and CD8+ cells. The CD25+ cells are probably also CD4+ and CD8+. Thus, T101 binds to cells that regulate the immune response.

Example 7

The purpose of the experiment was to examine how the T101 peptides influence the immune response in mice and whether the T101 peptide can influence any of the components of the immune system both with respect to the level of different cell types and in the ratio between different subpopulations.

Method 50 microgram/Kg of T101 peptide or saline were injected (twice a day for 8 days) into 7- to 8-week-old female Balb/C mice (10 mice per group). CDC analysis was made of the blood and the percentage of different subpopulations of white blood cells (WBC) (monocytes (MONO), lymphocytes (LYM) and total WBC (WBC)) was analyzed. Platelets and RBCs were used as controls.

Results

Figure 7:
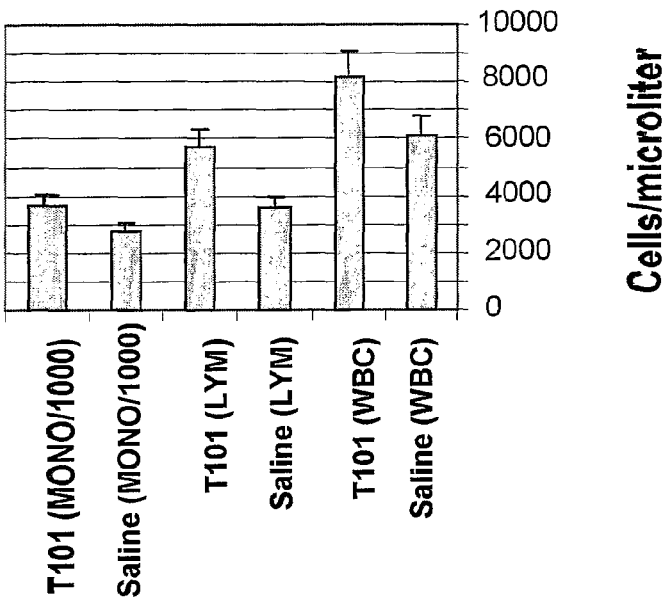
FIG. 7 is a bar graph showing cell count per microliter, of different human white blood cell populations—monocytes (MONO), lymphocytes (Lym) and whole white blood cell population (WBC)—following incubation of the cells in either saline containing T101 peptide (T101) or saline alone (Saline). The number of monocytes was divided by 1000 in order to include all of the results in one graph.

As shown in FIG. 7, in 7- to 8-week-old Balb/C female mice there was an increase of about 30% in total WBC following injection with the T101 peptide as compared to saline injection. When sub-populations of WBC were tested, there was an increase of about 30% in the lymphocytes and monocytes in the experimental group as compared to the saline injected control group.

Figure 8:
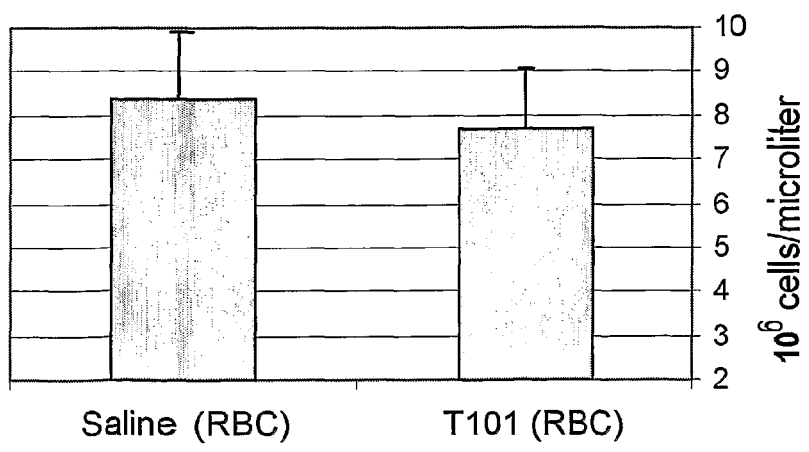
FIG. 8 is a bar graph showing cell count per microliter of human red blood cells following incubation of the cells in either saline containing T101 peptide (T101) or saline alone (Saline).

As a control, the levels of platelets and red blood cells (RBC) wore also examined. The difference between saline and T101 peptide injection was found to be less than 5%, as shown in FIG. 8 (results not shown for platelets).

Looking at CD4+ and CD8+ population did not reveal any significant differences between T101-treated mice and saline-treated mice (results not shown).

Figure 9:
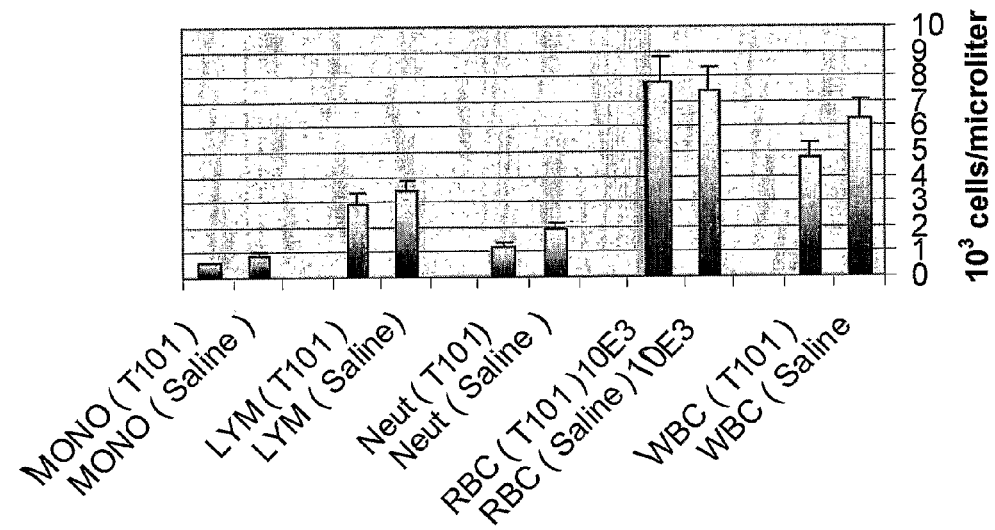
FIG. 9 is a bar graph illustrating cell count of different Balb/C blood cell populations: monocytes (Mono), Lymphocytes (Lym), Neutrophils (Neut), red-blood cells (RBC) and whole white blood cell population (WBC), following treatment of the animals with either T101 peptide or with saline (control).

This experiment was repeated in 3-4 week Balb/C females (7 mice in a group). The mice were injected with 72 microgram/Kg twice a day. The results are illustrated in FIG. 9.

In this experiment, as distinct from the above, the T101 peptide induced some suppression of the immune system as expressed in the level of the different cell types. The magnitude of the suppression was approximately 30%.

Example 8

The level of different subpopulations of cells in spleen lymphocytes was examined in Balb/C 3-to 4-week-old female mice, injected once a day with T101 (72 micrograms/Kg weight). The results are summarized in FIG. 10.

Figure 10:
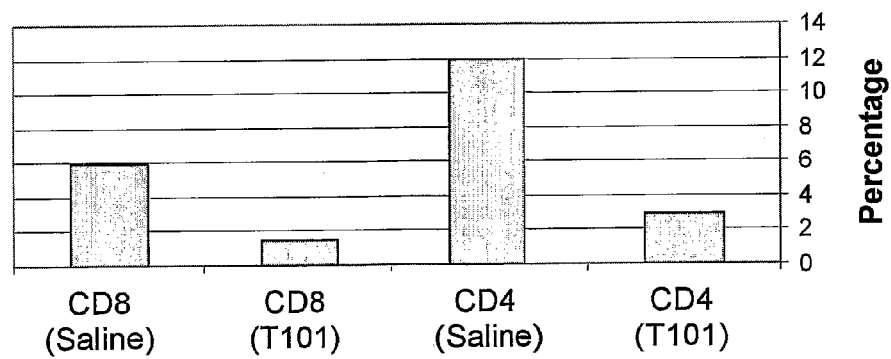
FIG. 10 is a bar graph showing cell count of CD4 and CD8 cells in Balb/C spleen lymphocytes following injection of the animals with either T101-containing saline or saline alone. The Y-axis shows % of the WBC.

As shown in FIG. 10, T101 decreased the levels of both CD4+ and CD8+ cells in the spleen of the mice. In thymus cells, there was no difference in the level of CD4+ and CD8+ cells (results not shown). In lymph node of the mice, a decrease in the range of 35-50% in the level of CD4+ cells was seen, but there was no change in CD8+ cells (results not shown).

Example 9

Figure 11:
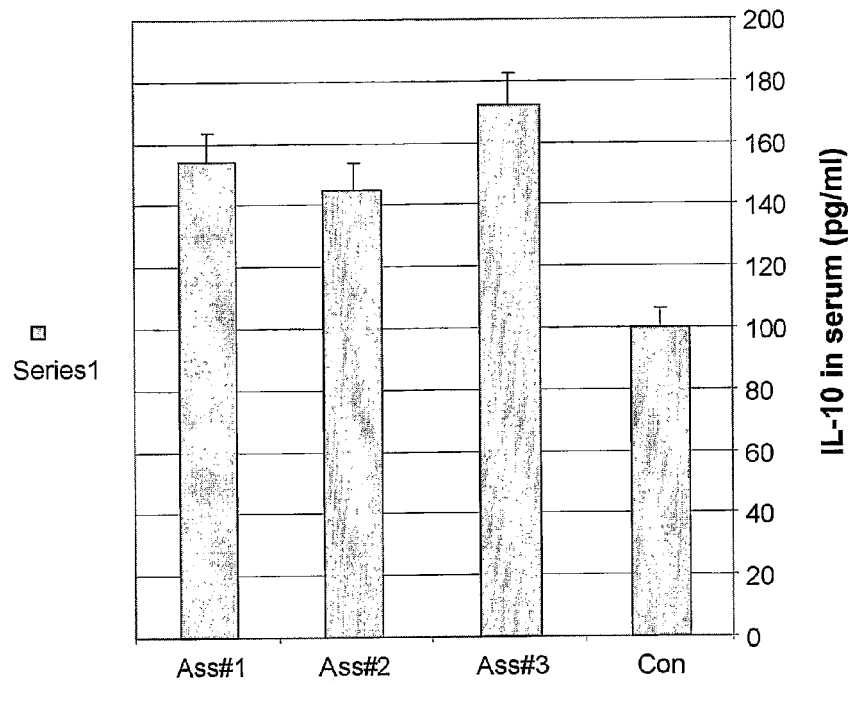
FIG. 11 is a bar graph showing IL-10 levels in mice injected with T101 in saline as compared to control of every other day saline injections. One experimental group received T101 peptide injection once every other day (Ass#1), a second group once daily (Ass#2) and a third group twice daily (Ass#3).

IL-10 is an interleukin that can suppress the immune system (TH2 interleukin). The level of IL-10 was assayed in three groups of 3 mice each: (1) one group of mice was injected with T101 twice a day (Assay #3); (2) another group was injected with the same concentration of T101 once a day (Assay #2); (3) the third group of mice was injected once every other day (Assay #1). All injected doses were thie same (72 micrograms/Kg weight). Mice injected with saline served as control (Con). The results are shown in FIG. 11.

As shown, the level of IL-10 was increased in all groups following the injection of T101 peptide to these mice. The best regimen of injections was once every other day.

These results are supportive for the use of T101 as an immune suppressor in the treatment of autoimmune diseases.

Example 10

In adult Balb/C mice, using lower concentrations of T101, some increase in the level of immune cells was observed. This experiment had the purpose of testing whether this increase can be applied to immunotherapy of cancer.

Method

Eight week Balb/C mice were injected with mammary carcinoma EMT6/CTX cells, and after the size of the tumor reached 4 mm$^2$, the mice were injected with T101 peptide (50 microgram/Kg) twice a day for 8 days. The size of the tumor was measured every other day as well as at the conclusion of the experiment.

Results

Figure 12:
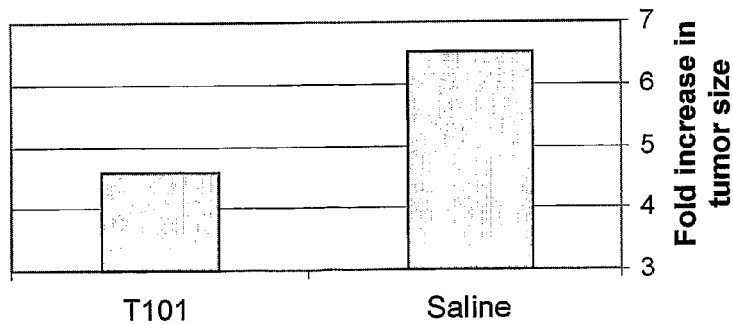
FIG. 12 is a bar graph showing the fold of increase in tumor size in Balb/C mice induced with mammary carcirioma and treated with either saline with T101 peptide or with saline alone.

The results regarding size of the tumor at day 14 are summarized in FIG. 12. In mice treated with the T101 peptide, the fold increase of the tumor size was 4.3, as compared to the original size of the tumor before injection. In mice that were treated with saline, the fold increase of the tumor size was 6.7. Thus, T101 was able to significantly reduce tumor growth.

Figure 13:
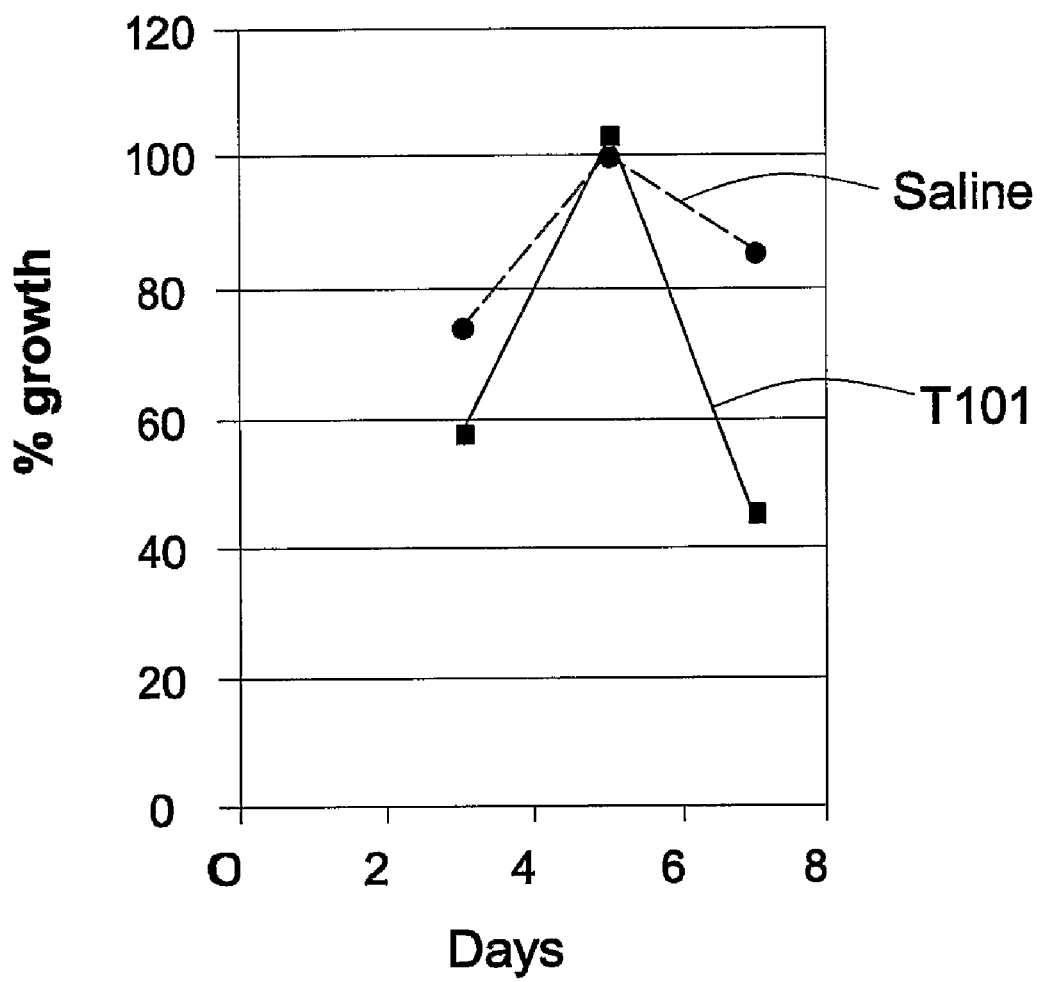
FIG. 13 is a graph showing the rate of growth (in %) of the tumor referred to in FIG. 12.

The rate of growth of the tumor is shown in FIG. 13. It can be seen that T101 was able to significantly decrease the growth rate of the tumor.

Pathological studies of these tumors revealed that in some of the T101-treated mice there was a significant increase in the numbers of lymphocytes and neutrophils in the tumor as compared with the control (results not shown).

These results indicate that T101 may be used therapeutically for cancer treatment.

Example 11

In order to test the ability of T101 to treat autoimmune diseases, a mouse model for colitis/Crohn's disease was used.

Eight-week-old female Balb/c mice received DSS (dextran sulfate) in the drinking water (5%) for 14 days. During that time the mice were injected with either saline or saline containing T101, in accordance with the below. Blood in the stool, body weight, and stool consistency were followed. At the end of the experiment the mice were sacrificed, the colon removed and its length measured.

The mice were divided into 4 groups, 3 mice per group:
- Group #1—Control—received normal drinking water (with no DSS) and without treatment.
- Group #2—DSS—received drinking water that contained 5% DSS and were injected with saline
- Group #3—DSS+BTL1—received drinking water that contained 5% DSS and were injected with T101 once every 3 days (at a dose of T101 of 52 microgram/Kg).
- Group #4—DSS+BTL2—received drinking water that contained 5% DSS and were injected with T101 once every 3 days (at a dose of T101 of 13 microgram/Kg).

Figure 14:
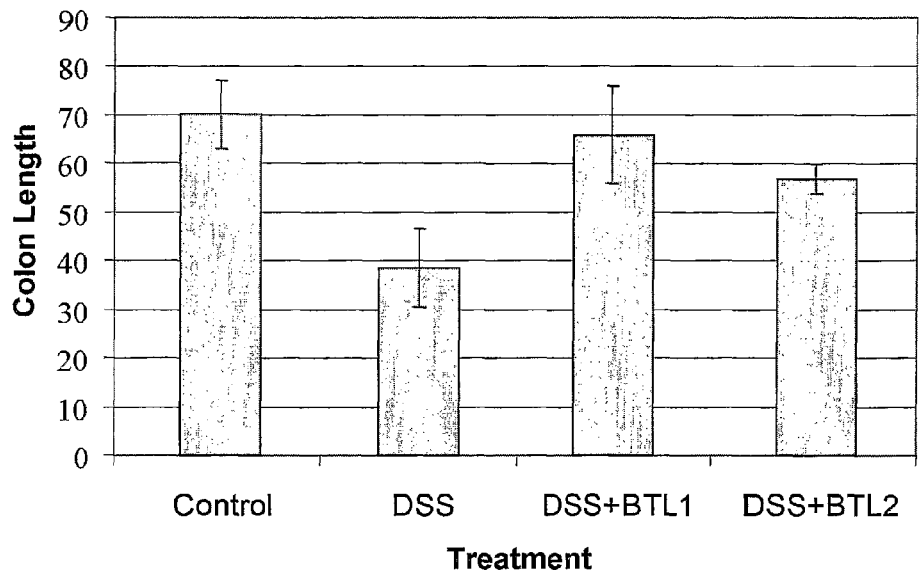
FIG. 14 is a bar graph showing the colon length of mice that received DSS through the drinking water and who were subsequently treated. Four groups of animals were tested: one group received no DSS and no treatment (Control); a second group received DSS in the drinking water and was treated with saline injection (DSS); the remaining two groups received DSS in the drinking water and were treated with injections of saline that contained 52 and 13 microgram/ml (DSS+BTL1 and DSS+BTL2, respectively).
Figure 15:
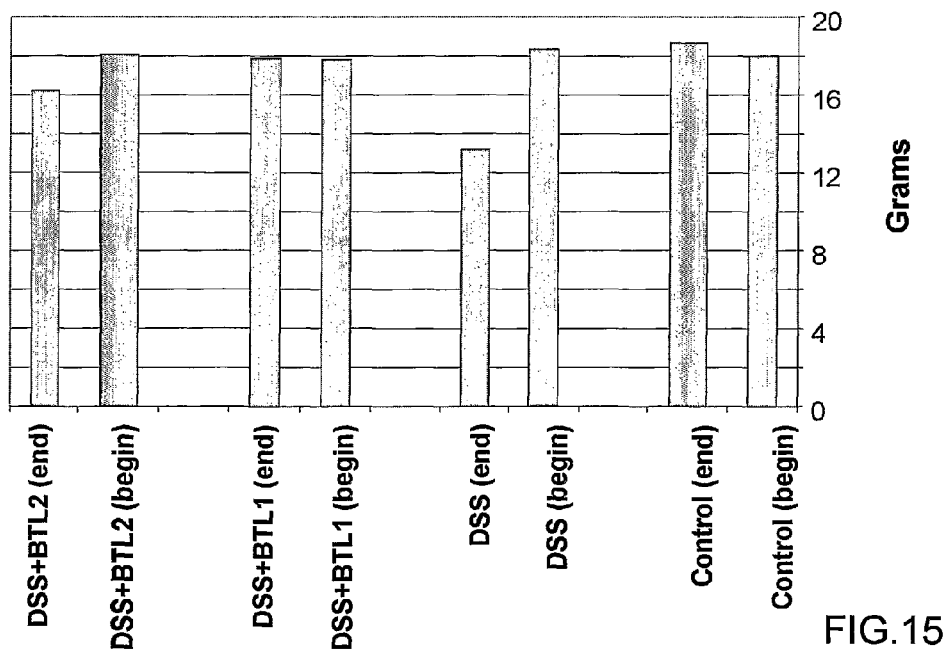
FIG. 15 is a bar graph which shows body weight of the mice of FIG. 14 that received DSS at the end of the experiment (end) versus the weight at the beginning (begin).

The results are summarized in FIGS. 14 and 15. It can be seen that the T101 peptide had a profound effect in decreasing disease symptoms in these animals, as compared with mice receiving DSS and only saline.

These results show that the T101 peptide can serve as an immunosuppressor in the treatment of autoimmune diseases such as colitis/Crohn's disease.

---

The invention claimed is:

1. An isolated polypeptide comprising the amino acid sequence of SEQ. ID. NO: 2 or the amino acid sequence of SEQ. ID. NO: 4.

2. An isolated polypeptide comprising a modified amino acid sequence of SEQ. ID. NO: 2 or SEQ. ID. NO: 4, in which one or more amino acid residues is added, deleted or replaced, without significantly affecting one or more biological characteristics selected from the group consisting of (a) stimulation of proliferation of mouse splenocytes or human peripheral blood lymphocytes (hPBL), (b) binding to hPBL, (c) modulating immune response, (d) increasing a level of IL-10, and (e) reducing tumor growth of an modified molecule as compared to an unmodified molecule, wherein at least 70% of the amino acids of SEQ. ID. NO: 2 or SEQ. ID. NO: 4 are left unsubstituted, and wherein the amino acid replacements are conservative substitutions.

3. The isolated polypeptide according to claim 2, comprising a sequence of amino acids $AA_1$ through $AA_{51}$ of SEQ. ID. NO: 4, wherein:

$AA_1$ is selected from leucine, isoleucine, valine and methionine;
$AA_2$ is selected from lysine, arginine and histidine;
$AA_3$ is selected from leucine, isoleucine, valine and methionine;
$AA_4$ is selected from tryptophan, phenylalanine and tyrosine;
$AA_5$ is selected from leucine, isoleucine, valine and methionine;
$AA_6$ is selected from serine, threonine, alanine, glycine and proline;
$AA_7$ is selected from serine, threonine, alanine, glycine and proline;
$AA_8$ is selected from glutamine, glutamic acid, aspartic acid and asparagine;
$AA_9$ is selected from serine, threonine, alanine, glycine and proline;
$AA_{10}$ is selected from leucine, isoleucine, valine and methionine;
$AA_{11}$ is selected from glutamine, glutamic acid, aspartic acid and asparagine;
$AA_{12}$ is selected from serine, threonine, alanine, glycine and proline;
$AA_{13}$ is selected from serine, threonine, alanine, glycine and proline;
$AA_{14}$ is selected from serine, threonine, alanine, glycine and proline;
$AA_{15}$ is selected from serine, threonine, alanine, glycine and proline;
$AA_{16}$ is selected from lysine, arginine and histidine;
$AA_{17}$ is selected from glutamine, glutamic acid, aspartic acid and asparagine;
$AA_{18}$ is selected from leucine, isoleucine, valine and methionine;
$AA_{19}$ is selected from lysine, arginine and histidine;
$AA_{20}$ is selected from serine, threonine, alanine, glycine and proline;
$AA_{21}$ is selected from lysine, arginine and histidine;
$AA_{22}$ is selected from serine, threonine, alanine, glycine and proline;
$AA_{23}$ is selected from glutamine, glutamic acid, aspartic acid and asparagine;
$AA_{24}$ is selected from serine, threonine, alanine, glycine and proline;
$AA_{25}$ is selected from lysine, arginine and histidine;
$AA_{26}$ is selected from lysine, arginine and histidine;
$AA_{27}$ is selected from leucine, isoleucine, valine and methionine;
$AA_{28}$ is selected from serine, threonine, alanine, glycine and proline;
$AA_{29}$ is selected from glutamine, glutamic acid, aspartic acid and asparagine;
$AA_{30}$ is selected from lysine, arginine and histidine;
$AA_{31}$ is selected from glutamine, glutamic acid, aspartic acid and asparagine;
$AA_{32}$ is selected from leucine, isoleucine, valine and methionine;
$AA_{33}$ is selected from leucine, isoleucine, valine and methionine;
$AA_{34}$ is selected from serine, threonine, alanine, glycine and proline;
$AA_{35}$ is selected from lysine, arginine and histidine;
$AA_{36}$ is selected from serine, threonine, alanine, glycine and proline;
$AA_{37}$ is selected from leucine, isoleucine, valine and methionine;
$AA_{38}$ is selected from tryptophan, phenylalanine and tyrosine;
$AA_{39}$ is selected from tryptophan, phenylalanine and tyrosine;
$AA_{40}$ is selected from serine, threonine, alanine, glycine and proline;
$AA_{41}$ is selected from tryptophan, phenylalanine and tyrosine;
$AA_{42}$ is selected from tryptophan, phenylalanine and tyrosine;
$AA_{43}$ is selected from leucine, isoleucine, valine and methionine;
$AA_{44}$ is selected from serine, threonine, alanine, glycine and proline;
$AA_{45}$ is selected from serine, threonine, alanine, glycine and proline;
$AA_{46}$ is selected from serine, threonine, alanine, glycine and proline;
$AA_{47}$ is selected from leucine, isoleucine, valine and methionine;
$AA_{48}$ is selected from tryptophan, phenylalanine and tyrosine;
$AA_{49}$ is selected from glutamine, glutamic acid, aspartic acid and asparagine;
$AA_{50}$ is selected from lysine, arginine and histidine; and
$AA_{51}$ is selected from lysine, arginine and histidine.

4. The isolated polypeptide according to claim 2, comprising a modified sequence of SEQ. ID NO: 2 or SEQ. ID. NO: 4, in which up to three residues are each substituted by another amino acid residue by conservative substitution.

5. The isolated polypeptide according to claim 2, comprising amino acid residues $AA_{38}$-$AA_{39}$-$AA_{40}$-$AA_{41}$-$AA_{42}$, being residues of positions 38 to 42 of SEQ. ID. NO: 4, which are either modified or unmodified, said modification being by conservative substitution, wherein:
- $AA_{38}$ is selected from tryptophan, phenylalanine, and tyrosine;
- $AA_{39}$ is selected from tryptophan, phenylalanine, and tyrosine;
- $AA_{40}$ is selected from threonine, serine, alanine and proline;
- $AA_{41}$ is selected from phenylalanine, tyrosine, and tryptophan;
- $AA_{42}$ is selected from phenylalanine, tyrosine, and tryptophan.

6. The isolated polypeptide according to claim 2, comprising amino acid residues $AA_{38}$-$AA_{39}$-$AA_{40}$-$AA_{41}$-$AA_{42}$-$AA_{43}$, being residues of positions 38 to 43 of SEQ. ID. NO: 4, which are either substituted by other amino acid residues or unsubstituted, said substitution being a conservative substitution, wherein:
- $AA_{38}$ is selected from tryptophan, phenylalanine, and tyrosine;
- $AA_{39}$ is selected from tryptophan, phenylalanine, and tyrosine;
- $AA_{40}$ is selected from threonine, serine, alanine and proline;
- $AA_{41}$ is selected from phenylalanine, tyrosine, and tryptophan;
- $AA_{42}$ is selected from phenylalanine, tyrosine, and tryptophan;
- $AA_{43}$ is selected from leucine, valine, isoleucine, and methionine.

7. The isolated polypeptide according to claim 2, comprising amino acid residues $AA_{36}$-$AA_{37}$-$AA_{38}$-$AA_{39}$-$AA_{40}$-$AA_{41}$-$AA_{42}$, being residues of positions 36 to 42 of SEQ. ID. NO: 4, which are either substituted by other amino acid residues or unsubstituted, said substitution being a conservative substitution, wherein:
- $AA_{36}$ is alanine;
- $AA_{39}$ is valine;
- $AA_{38}$ is selected from tryptophan, phenylalanine, and tyrosine;
- $AA_{39}$ is selected from tryptophan, phenylalanine, and tyrosine;
- $AA_{40}$ is selected from threonine, serine, alanine and proline;
- $AA_{41}$ is selected from phenylalanine, tyrosine, and tryptophan;
- $AA_{42}$ is selected from phenylalanine, tyrosine, and tryptophan.

8. The isolated polypeptide according to claim 2, comprising amino acid residues $AA_{36}$-$AA_{37}$-$AA_{38}$-$AA_{39}$-$AA_{40}$-$AA_{41}$-$AA_{42}$-$AA_{43}$, being residues of positions 36 to 43 of SEQ. ID. NO: 4, which are either substituted by other amino acid residues or unsubstituted, said substitution being a conservative substitution, wherein:
- $AA_{36}$ is alanine;
- $AA_{39}$ is valine;
- $AA_{38}$ is selected from tryptophan, phenylalanine, and tyrosine;
- $AA_{39}$ is selected from tryptophan, phenylalanine, and tyrosine;
- $AA_{40}$ is selected from threonine, serine, alanine and proline;
- $AA_{41}$ is selected from phenylalanine, tyrosine, and tryptophan;
- $AA_{42}$ is selected from phenylalanine, tyrosine, and tryptophan;
- $AA_{43}$ is selected from leucine, valine, isoleucine, and methionine.

9. The polypeptide sequence according to claim 2, wherein one or more amino acids are replaced by the corresponding D-amino acid.

10. An isolated polypeptide, comprising a contiguous sequence of 13 amino acid residues of SEQ. ID. NO: 4 and beginning from the C-terminal of SEQ. ID. NO: 4.

11. A method of treatment of a disease or disorder selected from the group consisting of an inflammatory condition, a cancer disease, and an autoimmune disease, comprising:
administering to a subject in need thereof, a therapeutically effective amount of the isolated polypeptide of claim 10.

12. An isolated polypeptide, comprising a sequence selected from the group consisting of SEQ. ID. NO: 5, SEQ. ID. NO: 7, SEQ. ID. NO: 9, and SEQ. ID. NO: 10.

13. An isolated protein or polypeptide comprising one of the following amino acid sequences: TABLE-US-00016 SKx$_1$x$_2$SDKQLISKAVx$_3$x$_4$x$_5$FFLx$_6$STL (SEQ ID NO: 15) SKx$_1$x$_2$SDKQLISKAV x$_3$x$_4$x$_5$FFLx$_6$ (SEQ ID NO: 16) SK x$_1$x$_2$SDKQLISKAVQRIFF, (SEQ ID NO: 17) or SK x$_1$x$_2$SDKQLISKAVQRIFFLx$_6$STL (SEQ ID NO: 18)
wherein $x_1$ represents R, Q, F, H, K, N, D, E, Y or W; $x_2$ represents V, M, I or L; $x_3$ represents W, Q, F, Y, N, D or E; $x_4$ represents W, R, F, Y, H or K; $x_5$ represents T, I, S, P, A, G, L, V or M; and $x_6$ represents P, L, S, T, A, G, I, V or M.

14. An isolated polypeptide, comprising a sequence selected from the group consisting of SEQ. ID. NO: 5, SEQ. ID. NO: 7, SEQ. ID. NO: 9 and SEQ. ID. NO: 10, wherein, in the sequence, one or more amino acids are replaced by the corresponding D-amino acid.

15. A pharmaceutical composition comprising the isolated polypeptide of claim 14.

16. A method of treating of a disease or disorder selected from the group consisting of an inflammatory condition, a cancer disease, and an autoimmune disease, comprising:
administering to a subject in need thereof, a therapeutically effective amount of the isolated polypeptide of claim 14.

17. An isolated polypeptide, comprising a contiguous sequence of 13 amino acid residues beginning from the C-terminal of SEQ. ID. NO: 4, wherein, in the sequence, one or more amino acids are replaced by the corresponding D-amino acid.

18. A pharmaceutical composition comprising the isolated polypeptide of claim 17.

* * * * *